United States Patent [19]

Sivam et al.

[11] Patent Number: 5,116,944
[45] Date of Patent: May 26, 1992

[54] CONJUGATES HAVING IMPROVED CHARACTERISTICS FOR IN VIVO ADMINISTRATION

[75] Inventors: Gowsala P. Sivam; A. Charles Morgan, Jr., both of Edmonds, Wash.

[73] Assignee: NeoRx Corporation, Seattle, Wash.

[21] Appl. No.: 459,068

[22] Filed: Dec. 29, 1989

[51] Int. Cl.⁵ .............................. C07K 17/02
[52] U.S. Cl. .................... 530/362; 530/363; 530/391.9; 530/402; 530/403; 530/391.7; 530/391.1; 530/866; 424/85.91
[58] Field of Search ............ 424/85.91, 94.3; 530/402, 362, 403, 388, 395, 408, 351, 381, 380, 399, 408, 387, 363, 389, 390, 391; 435/188, 391

[56] References Cited

U.S. PATENT DOCUMENTS

| | | | |
|---|---|---|---|
| 4,046,722 | 9/1977 | Rowland | 260/6 |
| 4,440,738 | 4/1984 | Fawzi et al. | 424/1.1 |
| 4,507,234 | 3/1985 | Kato et al. | 530/389 |
| 4,510,125 | 4/1985 | Grogg et al. | 424/1.1 |
| 4,545,985 | 10/1985 | Pastan et al. | 424/85 |
| 4,699,784 | 10/1987 | Shih et al. | 424/85 |
| 4,707,353 | 11/1987 | Bugaj et al. | 424/1.1 |
| 4,749,570 | 6/1988 | Poznansky et al. | 424/94.3 |
| 4,808,705 | 2/1989 | Ferris | 530/391 |
| 4,812,557 | 3/1989 | Yasushi et al. | 530/351 |
| 4,814,170 | 3/1987 | Karr et al. | 424/88 |
| 5,045,312 | 9/1991 | Aston et al. | 514/21 |

FOREIGN PATENT DOCUMENTS

| | | |
|---|---|---|
| 0314317 | 5/1989 | European Pat. Off. . |
| 0319944 | 6/1989 | European Pat. Off. . |
| 87/00406 | 8/1987 | PCT Int'l Appl. . |

OTHER PUBLICATIONS

Saelinger, "Trafficking of Bacterial Toxins," (CRC Press, Inc.) pp. 6-8,16,150-163 (1990).
Garnett et al., Int. J. Cancer, 31:661-670 (1983).
Kishore et al., Autoradiolysis of Iodinated Monoclonal Antibody Preparations, Nucl. Med. Biol., vol. 13, No. 4, pp. 457-459, 1986.

*Primary Examiner*—F. T. Moezie
*Assistant Examiner*—Andrew G. Rozycki

[57] ABSTRACT

Conjugates comprising a therapeutically effective proteinaceous active moiety linked to an albumin moiety which exhibit enhanced serum half-life and stability properties are disclosed. The conjugates may additionally comprise targeting moieties to facilitate selective localization of the active moiety at a target site. Conjugates of the present invention comprising an albumin moiety additionally exhibit reduced toxicity, yet maintain a high degree of selectivity and potency.

10 Claims, No Drawings

CONJUGATES HAVING IMPROVED CHARACTERISTICS FOR IN VIVO ADMINISTRATION

TECHNICAL FIELD

The present invention relates generally to conjugates which demonstrate enhanced efficacy for use in in vivo protocols where enhanced serum half-life and stability is desirable. The present invention relates more specifically to conjugates comprising proteinaceous therapeutic moieties which exhibit reduced toxicity in addition to increased serum half-life and serum stability, yet maintain a high degree of selectivity and potency.

BACKGROUND ART

Agents that are effective in killing neoplastic and other diseased or abnormal cells generally cannot be administered to a patient in effective doses because they also exert cytotoxic effects on normal cells. Therapeutic protocols for treating cancer and other disorders using cytotoxic agents such as toxins, drugs, radioisotopes, and the like are generally limited by the toxicity of the cytotoxic agent to normal cells and tissues. Efforts have therefore been directed to linking cytotoxic therapeutic agents to targeting agents, such as antibodies, which are capable of binding to certain target cells and tissue(s).

Research efforts in the field of tumor immunology have identified antibodies to antigenic determinants expressed preferentially on tumor cells. Such antibodies, or fragments thereof, may be employed as carriers for cytotoxic agents to provide selective delivery of cytotoxic agents to target tumor tissues. Therapeutic immunoconjugates comprising an active moiety exhibiting therapeutic properties and a targeting agent exhibiting specificity and affinity for target cells, tissue(s), antigens, or the like are believed to be of tremendous potential in the treatment of cancer and a variety of other diseases.

One type of conjugate thought to be potentially useful in the treatment of diseases such as cancer is an antibody-toxin conjugate consisting of a bacterial or plant toxin, or some portion thereof, covalently linked to an antibody. Initially, such immunoconjugates comprised reduced and sulfhydryl activated polyclonal antibodies linked to reduced toxins. This method of conjugation was relatively uncontrolled and unpredictable, since antibody and toxin disulfide bonds could reform as readily as antibody-toxin hybrids. Heterobifunctional reagents having two different reactive end groups were subsequently developed and became preferred compounds for linking antibodies to toxins. Using heterobifunctional reagents, the number of free sulfhydryl groups available for conjugation, and ratios of antibody to toxin in the immunoconjugate product, could be controlled fairly effectively. The presence of two different reactive groups on heterobifunctional reagents permitted more directed, predictable, and reproducible linkage of targeting agents to cytotoxic agents. Numerous heterobifunctional reagents have been reported in the literature for derivatizing antibody and/or toxin molecules.

Coupling the targeting agent of an immunoconjugate to a toxin moiety through disulfide bonds which can be reductively cleaved may be achieved employing various heterobifunctional reagents. Using other heterobifunctional reagents, targeting and active moieties may be covalently linked through bonds that are not affected by reducing agents, such as amide or thioether bonds. Disulfide-bonded toxin immunoconjugates were initially believed to be necessary to mimic the disulfide linkage of A and B chains of native toxin. It was thought that the native disulfide linkage had to be reductively cleaved to liberate the active A chain of the toxin molecule within the cell. Linkage of A chains of toxins with antibodies through non-reducible bonds generally produced immunoconjugates of decreased potency. Immunoconjugates of Pseudomonas exotoxin (PE) coupled to monoclonal antibodies (MAbs) or to epidermal growth factor (EGF) are disclosed in U.S. Pat. No. 4,545,985 (I. Pastan et al., 1985).

The serum half-life of therapeutic agents such as immunoconjugates may directly impact and may be related to numerous factors affecting the efficiency of therapeutic protocols. Enhancement of serum half-life is an important objective since, in general, the longer therapeutic agents remain in circulation, the higher the likelihood they will reach target cells and tissue(s).

Antibody fragments may offer advantages as the targeting component in immunoconjugate compounds since antibody fragments accumulate at target sites, such as tumor sites, more rapidly than their whole antibody counterparts. Rapid localization may be due to the smaller size of the fragments. In addition, decreased fragment size may facilitate egress from circulation across the blood vessel and capillary walls into the tumor bed. However, the smaller fragments generally have shorter serum half-lives than whole antibody, and the increased rapidity of target tissue localization may not offset the reduced serum half-life characteristics of the immunoconjugates. That is, conjugates comprising antibody fragments may be cleared prior to tumor localization, despite their increased tumor localization capability. Thus, it would be desirable to prolong serum half-life of conjugates comprising relatively small targeting moieties, such as antibody fragments, to take advantage of their target site localization characteristics.

Moreover, clearance of therapeutic agents such as immunoconjugates from circulation is generally harmful, since high concentrations of the active (typically cytotoxic) moiety accumulate in non-target tissues and destroy tissue at those non-target sites. Still further, when significant quantities of therapeutic agents are removed from circulation before they reach the target site(s), higher doses are required to produce the desired diagnostic or therapeutic effect. Higher doses in turn cause more damage to normal tissues and generally cannot be tolerated due to the accompanying adverse side effects.

Providing enhanced serum stability of therapeutic agents is another important objective. Immunoconjugates comprising an active moiety bound to a targeting moiety must remain stably bound in serum for sufficient time to allow the targeting moiety to selectively deliver the active moiety to the target site. If the bond(s) linking the active and targeting moieties are not sufficiently stable, the targeting moiety may become detached from the active moiety before it has reached the target site, thereby contributing to non-target retention of the active agent and resultant toxicity.

Effective doses of therapeutic drugs, such as anti-cancer drugs, typically require administration of fairly large quantities of drug. In many cases, it is difficult to administer an effective dose of a therapeutic drug unless multiple molecules of the drug are bound to each carrier moiety. Binding multiple drug molecules to a targeting agent is difficult to accomplish however, without impairing the target specificity of the targeting agent or the activity of the drug. Drug carrier intermediates are frequently employed, whereby a plurality of drug molecules is bound to the intermediate, and the intermediate is bound to the targeting moiety. In this fashion, multiple drug molecules may be associated with a single targeting agent without impairing the specificity of the targeting agent. Human serum albumin (HSA) and other molecules have been used as intermediate drug carriers. U.S. Pat. Nos. 4,507,234; 4,046,722; 4,699,784; and Garrett et al., Int. J. Lancer 31:661-670 (1983), describe immunoconjugates in which a drug carrier is interposed between the active moieties and targeting agents to provide higher drug loading.

HSA has also been suggested as a targeting agent for bone imaging agents comprising diagnostic radionuclides to facilitate delivery of the diagnostic agent to soft tissues and blood pool visualization. Diagnostic imaging agents optionally including HSA are taught in U.S. Pat. Nos. 4,440,738, 4,510,125 and 4,707,353.

HSA has been employed as a stabilizing agent for various compositions intended for in vivo administration. For example, U.S. Pat. No. 4,812,557 teaches use of HSA for stabilizing interleukin-2 (IL-2) compositions during storage, freezing, and/or lyophilization. HSA has also been utilized as a stabilizer for radio-iodinated compositions to prevent the loss of immunoreactivity and to protect and stabilize therapeutic quantities of radio-iodinated monoclonal antibody preparations. In these latter applications, HSA is present in solution, but it is not linked to an active or targeting moiety.

SUMMARY OF THE INVENTION

Conjugates according to the present invention comprise a therapeutically effective proteinaceous active moiety such as a protein toxin, toxin fragment, biologic response modifier, receptor, or the like, linked to an albumin moiety. Conjugates of the present invention may additionally comprise targeting moieties which preferentially bind to target cells, tissue(s), receptors and/or antigenic determinants associated with such target cells or tissue(s), and which thereby facilitate localization of the active moiety at the target site.

In addition to extended serum half-life properties, conjugates of the present invention exhibit increased solubility and reduced toxicity compared to those properties exhibited by immunoconjugates or active moieties alone. The albumin moiety may function to mask the proteinaceous active moiety, thereby reducing receptor mediated uptake of such moieties and conjugates at non-target sites, such as the reticuloendothelial system. Blocked receptor uptake frees the active moiety or immunoconjugate to remain in circulation, rather than accumulate in non-target reticuloendothelial cells.

The albumin moiety may be bound to the active moiety and/or targeting moiety by means which are known in the art. It is, of course, important that binding of the component moieties of the conjugate is accomplished without significantly reducing the activity or target selectivity of the component moieties. Covalent bonds such as thioether, amide, ester, and the like are preferred.

DESCRIPTION OF PREFERRED EMBODIMENTS

Conjugates according to the present invention comprise a proteinaceous active moiety, such as a biologic response modifier, protein toxin or fragment thereof, receptor, other proteinaceous active moiety, or the like, linked to an albumin moiety. Where the active moiety comprises a protein toxin or fragment thereof, another therapeutically effective proteinaceous active moiety, or the like, conjugates of the present invention preferably additionally comprise a targeting moiety which provides selective delivery of the active moiety to a predetermined target site.

Albumin moieties suitable for use in conjugates according to the present invention include whole (native) human serum albumin (HSA) and albumin from other sources which exhibits similar serum half-life enhancement properties. Albumin and fragments thereof derived from natural as well as engineered sources may be used. Proteinaceous moieties having primary, secondary and tertiary structures substantially similar to HSA isolated from human serum are preferred. Albumin moieties may also comprise modified forms of albumin having an altered primary, secondary, tertiary or quaternary structure which exhibit properties similar or superior to native (whole or fragmented) albumin, as well as albumin derivatives comprising, for example, functionally important HSA domains. Albumin moieties may also comprise "refolded" albumin, as disclosed in this specification, which may have a secondary and/or tertiary and/or quaternary structure different from that of native albumin.

Albumin moiety domains which are responsible for conferring enhanced serum half-life and solubility and reduced toxicity properties may, for example, be isolated and engineered to be expressed directly as fusion proteins in accordance with the practice of the present invention. Toxin A chain/albumin domain fusion proteins and receptor CD4/HSA fusion proteins would be exemplary of such an embodiment. Other serum glycoproteins which exhibit extended serum half-lives may be utilized in the place of albumin, and are encompassed within the term "albumin moiety," to provide conjugates having enhanced serum half-lives and reduced toxicity. Suitable serum glycoproteins include alpha-2 macroglobulin, orosomucoid, and other stable serum glycoproteins. The serum constituent used is preferably homologous to the mammal intended as the recipient.

"Active" moieties as used herein include therapeutically effective proteinaceous moieties which are administered alone or bound to other components, such as targeting moieties, to produce a therapeutic effect. According to broad aspects of the present invention, any proteinaceous active moiety for which prolonged serum half-life or stability, or reduced toxicity is desired, may be linked to an albumin moiety to provide a conjugate having improved characteristics. Therapeutically effective active moieties suitable for use in the present invention include biologic response modifiers, protein toxins and fragments or components thereof, receptors such as soluble CD4, as well as other proteinaceous cytotoxic substances.

Activity, as well as targeting functions, may be conferred by biologic response modifiers. Suitable biologic response modifiers for use in the present invention include lymphokines, such as colony stimulating factors, including macrophage colony stimulating factor (M-

CSF), granulocyte colony stimulating factor (G-CSF), and granulocyte macrophage colony stimulating factor (GM-CSF); lymphotoxins; interleukins, including IL-1, -2, -3, -4, -5, -6, -7 and -8; interferons, including alpha, beta, and gamma interferons; tumor necrosis factor; erythropoietin; growth factors; as well as other cytokines; clotting factors such as plasminogen activator; urokinase; and the like. Active moieties suitable for use in the present invention are characterized by their relatively short serum half-lives resulting, at least in part, from receptor-mediated uptake by non-target organs and/or premature excretion through the kidneys.

Conjugates of the present invention may comprise biologic response modifiers having an albumin moiety bound thereto to provide enhanced serum half-life and solubility properties. Albumin moieties are preferably linked to biologic response modifiers, such as lymphokines and cytokines, by means of thioether bonds, although other types of bonds may be employed. For example, albumin may be derivatized by reaction of a free $NH_2$ group with the activated ester moiety of a heterobifunctional reagent such as SMCC. A free sulfhydryl group may be generated on the biologic response modifier by reducing a native disulfide bond. The derivatized albumin may then be linked to the biologic response modifier by reaction of the free sulfhydryl group with the maleimide or other appropriate reactive moiety of the heterobifunctional reagent. Alternatively, the biologic response modifier may be derivatized using a heterobifunctional reagent such as SMCC; a free sulfhydryl group may be generated by reducing a native disulfide bond on the albumin moiety; and the derivatized biologic response modifier linked to the albumin moiety by reaction of the free sulfhydryl group with a maleimide or other appropriate reactive moiety of the heterobifunctional reagent.

Conjugates according to the present invention may also comprise immunoconjugates linked to albumin moieties. The term "immunoconjugate," as used herein, refers to an active moiety linked to a targeting moiety capable of selective delivery of the active moiety to a predetermined target site. Preferred active moieties include, generally, therapeutically effective proteinaceous moieties such as protein toxins, toxin fragments, and other proteinaceous active moieties. Targeting moieties suitable for use in the present invention include, generally, immunoglobulins, native as well as modified antibodies and fragments thereof, biologic response modifiers, and the like, as well as a variety of carbohydrates such as polysaccharides, glycoproteins targeted to endogenous lectins or receptors such as mannose receptors, or other compounds having a carbohydrate moiety.

Preferred protein toxins which may be employed as active moieties in conjugates of the present invention include ricin, abrin, diphtheria toxin, Pseudomonas exotoxin A (PE), and ribosomal inactivating proteins such as gelonin, pokeweed antiviral protein and saporin. PE is an especially preferred protein toxin moiety. Soluble CD4 is an especially preferred protein receptor which may be employed as an active moiety in conjugates of the present invention. Therapeutically effective toxins and receptors, or fragments thereof, as well as modified toxins and receptors, and fragments thereof, such as those produced by means of genetic engineering or protein engineering techniques, may also be used.

Targeting moieties provide selective delivery of an active moiety to a receptor, substrate, cell surface membrane, antigenic determinant associated with such receptor, substrate or cell surface membrane, or other site in proximity to the target cells or tissue(s). Suitable targeting moieties include, but are not limited to, antibodies and fragments thereof, receptors (particularly cell surface receptors such as lectins), enzymes (e.g., fibrinolytic enzymes), biologic response modifiers (e.g. interleukins, interferons, erythropoietin, or colony stimulating factors), peptide hormones, and fragments thereof. These proteins may be modified to produce variants, derivatives, fragments, or the like, as long as the desired binding activity is retained. Targeting moieties may be produced and/or modified using various genetic engineering and/or protein engineering techniques, or by chemical modification. Binding of the reactive moiety to the targeting moiety to provide an immunoconjugate may be accomplished by techniques which are known in the art, and specific preferred embodiments will be described in detail below.

According to preferred embodiments of the invention, the targeting moiety preferably comprises a monoclonal antibody or a fragment thereof. Numerous monoclonal antibodies (MAbs) that bind to or associate with specific types of target cells have been developed, including MAbs specific for tumor-associated antigens in humans. Among the many such MAbs that may be used are anti-TAC, or other interleukin-2 receptor antibodies; 9.2.27 and NR-ML-05 to the 250 kd human melanoma-associated proteoglycan; NR-LU-10 to the 37-40 kd pancarcinoma glycoprotein; NR-CO-02 having colon specificity; and $OVB_3$ to an as yet identified tumor-associated antigen.

Antibodies derived or modified using genetic or protein engineering techniques may be employed as well. Antibodies utilized in the present invention may be intact molecules, fragments thereof, or functional constituents or equivalents thereof. Antibody fragments such as Fab, Fab', F(ab')$_2$, Fv, single chain antibody fragments, and the like may be preferred for various applications. Chimeric antibodies which have a functional variable region derived from one source and a constant region derived from a different source (e.g., species or isotype class) may also be used. Engineered antibodies referred to as single chain antibodies may be used.

According to preferred embodiments of the present invention, the albumin moiety (e.g., HSA) is preferably bound to the active moiety (AM) and/or the targeting moiety (TM) in one of the configurations shown below:

TM-AM-hSA; or HSA-TM-AM; or HSA-TM-AM-HSA That is, the albumin moiety is coupled to the active moiety and/or the targeting moiety to provide as great as possible surface area contact between the albumin moiety and intra- and extra-cellular fluids. Molar ratios of approximately 1:1:1, TM:AM:HSA, are preferred, and may be achieved using appropriate heterobifunctional reagents and purification techniques. Immunoconjugates may be formed and an albumin moiety subsequently linked to the targeting and/or active moiety constituent thereof or, alternatively, an albumin moiety may be linked to a targeting or active moiety, which is subsequently linked to the other immunoconjugate constituent.

Although conjugates according to the present invention may be arranged so that the albumin moiety is bound to the targeting moiety, it is preferred that the albumin moiety is bound to the active moiety so that if the active moiety is cleaved from the targeting moiety after delivery to the target site, the albumin moiety still imparts enhanced solubility and reduced toxicity to the active moiety. Alternatively, albumin moieties may be bound to both the active moiety and the targeting moiety. Care must be exercised in binding constituents to the targeting moiety to p-reserve the selectivity and binding properties of the targeting moiety.

In addition, it is preferred that the albumin moiety is bound in such a manner as to be in close physical proximity to the active moiety. Close physical proximity of the albumin moiety serves to mask the portions of the active or targeting moiety which are capable of interacting with and binding to non-target receptors, such as those found on reticuloendothelial cells. As a result, the active moiety or conjugate will not bind so readily at non-target sites, but rather will remain in circulation so that delivery to target sites may occur.

Numerous methods for binding active moieties to targeting moieties to produce immunoconjugates are known in the art. Therapeutically effective proteinaceous active moieties, such as protein toxins, may be coupled to targeting moieties directly or through the use of homo- or heterobifunctional reagents. Immunoconjugate components may be linked by means of readily cleavable disulfide bonds, or less readily cleavable thioether or amide bonds, or the like. Immunoconjugates comprising protein toxin moieties linked to targeting moieties by means of stable thioether bonds are preferred for use in the present invention. Additionally, according to especially preferred embodiments, albumin moieties of conjugates of the present invention are coupled to the active and/or targeting moieties of immunoconjugates by means of thioether bonds.

One preferred method for binding proteinaceous active moieties such as protein toxins to targeting moieties is described in copending U.S. patent application No. 07/095,178, filed Sep. 10, 1987,now U.S. Pat. No. 4,981,979, incorporated herein by reference in its entirety. A preferred conjugation methodology generally comprises heterobifunctional reagent, such as succinimidyl 4-(N-maleimidomethyl) cyclohexane-1-carboxylate (SMCC), or derivatives thereof, which have a malemide group at one end and an activated ester group at the other end. The proteinaceous active moiety is derivatized by nucleophilic attack at the activated ester. The targeting agent, generally an antibody or fragment thereof, is typically treated with a reducing agent such as dithiothreitol (DTT), or the like to produce a free sulfhydryl group from a native disulfide bond. Following separation of the derivatized proteinaceous active moiety from the reaction mixture containing it, reduced targeting agent is incubated with the derivatized protein. The targeting agent is covalently linked to the active moiety by reaction of the sulfhydryl group with the maleimide group of the heterobifunctional reagent to form an immunoconjugate joined by a thioether bond. Preferred heterobifunctional reagents include SMCC and derivatives thereof. Preferred reducing agents include dithiothreitol (DTT), and the like.

Disulfide bonded immunoconjugates may be produced in accordance with a modified methodology based upon that of R. Pirker et al., *J. Clin. Invest.*, 76:1261 (1985). In general, both targeting agent and active agent are reacted with an excess of 2-iminothiolane (2-IT) (i.e., approximately 1:5 ratio of protein:reagent). Unreacted molecules are then removed by any viable separation technique, such as gel filtration. The derivatized targeting agent (i.e., antibody derivatized with 2-IT) is then reacted with dithiobis-(2-nitrobenzoic acid) (DTNB). Excess DTNB is removed and the antibody—(2-IT)—DTNB derivative is then incubated with the active agent—(2-IT) derivative at room temperature to form a disulfide-linked immunoconjugate.

Alternatively, when the targeting agent has a carbohydrate moiety, derivatization may involve chemical treatment of the carbohydrate, such as glycol cleavage of the sugar moiety of a glycoprotein antibody with periodate to generate free aldehyde groups. The generated free aldehyde groups on the antibody may be reacted with free amine or hydrazine groups on the active or HSA moiety to bind the active or HSA moiety thereto.

Modified, non-native proteins, including refolded holotoxins and refolded albumin, may be incorporated in the conjugates of the present invention. Refolded proteinaceous active agents may exhibit a secondary and/or tertiary and/or quarternary structure different from that of the native protein and retain substantially all of at least one desired biological activity, such as translocating and/or enzymatic activity, yet experimental evidence indicates they exhibit reduced toxicity. Experimental studies also indicate that refolded proteins are generally less immunogenic than their native counterparts. Refolded proteins such as holotoxins and albumin may be produced by contacting the protein with a denaturing agent (and a reducing agent when the protein contains intrachain disulfide bonds) in an amount sufficient to promote unfolding or disruption of the secondary, tertiary and quaternary structures of the protein. The unfolded protein is then incubated under conditions which promote refolding thereof into a conformation wherein the refolded protein has reduced toxicity, but retains the desired biological activity (e.g. translocating and/or enzymatic activity). A charged, amphipathic compound may be employed to promote refolding of the protein in a non-native conformation. Methods for denaturing and refolding proteins to non-native conformations wherein the refolded protein has reduced toxicity, yet retains its biological activity are described in copending U.S. patent application Ser. Nos. 07/330,848 and 07/414,883, filed Mar. 29, 1989 and Sep. 29, 1989, respectively, which are incorporated herein by reference in their entirety.

The following examples set forth specific conjugates and their methods of manufacture for the purpose of more fully understanding preferred embodiments of the present invention, and are not intended to limit the invention in any way.

EXAMPLE I

Preparation of Disulfide-Linked and Thioether-Linked Immunoconjugates

Disulfide-bonded (cleavable) protein toxin immunoconjugates were produced by a modification of the method of R. Pirker et al., *J. Clin. Invest.* 76:1261, 1985 using anti-TAC monoclonal antibodies (MAbs). Briefly, both monoclonal antibody and Pseudomonas exotoxin A (PE) were reacted with 2-iminothiolane in a molar ratio of 1:5 (protein:reagent). Unreacted MAb and toxin molecules were removed by gel filtration, and derivatized anti-TAC MAbs were reacted with dithiobis(2-nitrobenzoic acid) (DTNB). Excess DTNB was removed, and DTNB-anti-TAC was reacted with derivatized PE (Ab:toxin offering ratio of 1:3) at room temperature for up to four hours.

PE was conjugated to NR-LU-10 MAb by means of a thioether linkage. The PE was first reacted with the heterobifunctional reagent succinimidyl 4-(N-maleimidomethyl)cyclohexane-1-carboxylate (SMCC) at a molar ratio of 1:10 (protein:reagent). Excess unreacted heterobifunctional reagent was removed from derivatized PE by gel filtration. NR-LU-10 was treated with 25 mM dithiothreitol (DTT) in 0.1 M phosphate-buffered saline, pH 7.5 (PBS), and excess unreacted DTT was removed by gel filtration. The derivatized toxin and the reduced antibody components were mixed (antibody:toxin offering ratio of 1:1) and incubated at room temperature for about 15 minutes.

Both disulfide-bonded and thioether linked conjugation reaction mixtures-1 were fractionated by FPLC gel filtration of a TSK 3000 column at 0.5 ml/min to separate immunoconjugates from unconjugated antibody and unreacted derivatized PE. The disulfide-linked conjugate species were distributed over a broad range of sizes, which corresponded to molar ratios of PE:-MAb of 3:1 and higher, 2:1 and 1:1. The preferred species of immunoconjugate is generally characterized by a 1:1 PE:MAb ratio. Disulfide conjugation provided a 1:1 PE:MAb conjugate yield of about 30%. The thioether-linked conjugation mixture was fractionated into relatively narrower size ranges, which primarily corresponded to a 1:1 molar ratio of PE:MAb. The yield of 1:1 conjugates was approximately 80%. The data indicate that formation of thioether linked protein toxin/antibody conjugates is significantly more efficient than formation of disulfide-linked conjugates for production of the desired 1:1 toxin:antibody conjugate species.

EXAMPLE II

Conjugation of HSA to Disulfide-linked Immunoconjugates.

Albumin may be linked to either the antibody or the protein toxin component of the disulfide-linked Immunoconjugates prepared in Example I. To link the HSA moiety to the antibody constituent, HSA was derivatized by reaction with 2-iminothiolane in a molar ratio of 1:10 (protein:reagent), and excess reagent was removed by gel filtration. Derivatized HSA was mixed with the immunoconjugate reaction components and incubated at room temperature for at least two hours. Conjugates comprising disulfide-linked immunoconjugates having HSA moieties linked to the antibody constituent were fractionated by FPLC (gel filtration).

HSA was linked to the toxin moiety of disulfide-linked immunoconjugates prepared as described in Example I by reaction HSA with 2-iminothiolane in a molar ratio of 1:10 (protein:reagent) for 30 minutes. Excess DTNB was added, and the reaction mixture incubated for an additional 10 minutes. Excess reagents were removed by gel filtration and derivatized HSA was incubated with the immunoconjugate reaction components for about two hours. Conjugates comprising disulfide-linked immunoconjugates having HSA moieties linked to the toxin constituent were fractionated.

Conjugation of HSA to Thioether-linked Immunoconjugates

Albumin may be linked to either the antibody or protein toxin constituent of the thioether-linked immunoconjugates prepared in Example I. To link HSA to the antibody constituent, HSA was derivatized by reaction with SMCC in a molar ratio of 1:10 (protein:- reagent) for 30 minutes, and excess reagent was removed. The derivatized HSA was mixed with the immunoconjugate reaction components 15 minutes after the conjugation reaction was initiated, and the conjugation reaction components were incubated for an additional 30 minutes. The conjugation reaction mixture was fractionated by FPLC (gel filtration) to yield conjugates having HSA linked to the antibody constituent in a ratio of 1:1:1, HSA:MAb:PE.

HSA was linked to the toxin constituent of thioether-linked immunoconjugates prepared as described in Example I by reacting HSA with 2-iminothiolane in a molar ratio of 1:10 (protein:reagent) for 30 minutes. Excess reagent was removed by gel filtration, and derivatized HSA was mixed with the immunoconjugate reaction components 15 minutes after the conjugation reaction was initiated. The conjugation reaction components were incubated for an additional 30 minutes, and the reaction mixture was fractionated to yield conjugates having HSA linked to the toxin constituent of the immunoconjugate in a ratio of 1:1:1, HSA:PE:MAb.

EXAMPLE III

Immunoconjugates Containing Refolded PE

Refolded PE was synthesized from native PE as follows. Native PE (10 mg) in phosphate buffered saline (100 mM $PO_4^{3-}$, 0.12% NaCl) was treated With urea (4M) and dithiothreitol (100mM DTT). The reaction mixture was agitated on a rotary shaker at room temperature. After about 120 minutes, the reaction mixture was subjected to size exclusion gel filtration on a PD-10 column (Pharmacia) to yield unfolded PE (about 8.5 mg). This material was dialyzed against PBS (1 liter) overnight to remove traces of urea and DTT. Unfolded PE was then treated with 1% sodium dodecyl sulfate (SDS) in a final concentration of 0.1% SDS. Several samples of the mixture were incubated at pHs of 4.5, 5.5, 6.5, 7.5 and 8.5 at room temperature for up to 4–5 hours, and then stored at 4° C. overnight. The refolding reaction was monitored by FPLC on a Superose-12 gel filtration column. Monitoring indicated that refolding can be accomplished at a pH of about 7.5 to 8.5 for about 1–2 hours. The refolded PE may optionally be stabilized by addition of 5,5'-Dithio Bis-(2-nitro) benzoic acid (DTNB, 1:1) or N-succinimidyl 3-(2-pyridyldithio) propionate (SPDP, 1:2).

For conjugation, refolded PE was first reacted with succinimidyl-4-(N-maleimidomethyl)cyclohexane-1-carboxylate (SMCC) at a molar ratio of 1:10 (protein:SMCC) at pH 8.5 and agitated at room temperature for 30 minutes. Excess unreacted heterobifunctional reagent (SMCC) was removed from derivatized PE by gel filtration. Whole NR-LU-10 was treated with 25 mM dithiothreitol (DTT) in 0.01 M phosphate-buffered saline, pH 7.5, and excess DTT was removed by gel filtration. The derivatized toxin and the reduced antibody components were mixed and incubated at room temperature for at least 15 minutes. Conjugation reaction mixtures were fractionated by FPLC gel filtration on a Superose 12 gel filtration column to separate the conjugated product from unconjugated antibody and unreacted derivatized PE. Refolded PE/MAb conjugates were linked to HSA according to the protocol described in Example II.

EXAMPLE IV

Refolded HSA

Native HSA in phosphate buffered saline at pH 7.5 was treated with urea (4M) and DTT (100 mM), and the reaction mixture was agitated for about 120 minutes at room temperature. The reaction mixture was then subjected to size exclusion gel filtration on a PD-10 column to yield unfolded HSA. After gel filtration, SDS was introduced to give a final concentration of 0.1% SDS. 5,5'-Dithio Bis-(2-nitro) benzoic acid (DTNB 1:1) was then added to promote the reformation of the interior disulfide bonds in the structure of HSA. Refolded HSA was then linked to toxin/MAb conjugates according to the protocol described in Example II.

EXAMPLE V

Serum Half-life Studies

Immunoconjugates comprising NR-LU-10:PE and NR-LU-10(Fab):PE were prepared in accordance with the thioether linkage protocol outlined in Example I. Conjugates comprising HSA were prepared in accordance with the general protocol outlined in Example II.

Test samples including whole MAb (NR-LU-10); MAb fragment (NR-LU-10(Fab)); MAb/toxin immunoconjugates (NR-LU-10:PE); MAb fragment/HSA conjugates (NR-LU-10(Fab):HSA) and immunoconjugate/HSA conjugates (NR-LU-10(Fab):HSA:PE) were the subject of serum half-life studies conducted in mice. The test samples were radiolabeled and injected into mice. Blood samples were withdrawn at various time intervals and counted to determine the amount of radiolabel in circulation. The data presented in Table 1 is indicative of the serum concentrations of the test samples over time. AUC is the area under a curve plotting percent injected dose remaining in serum against time. A higher value for AUC indicates a longer serum half-life because the material remained in the serum at higher concentrations over the 24 hour time period tested.

TABLE 1

| Test Material | AUC* |
|---|---|
| NR-LU-10 | 924.41 |
| NR-LU-10(Fab) | 57.16 |
| NR-LU-10(Fab):HSA | 881.61 |
| NR-LU-10:PE | 767.12 |
| NR-LU-10(Fab):PE | 117.32 |
| NR-LU-10(Fab):HSA:PE | 160.67 |

*Area Under Curve plotting percent injected dose remaining in serum on Y axis and time on the X axis.

As Table 1 indicates, Fab antibody fragments cleared from the serum much more rapidly than whole antibody. Whole NR-LU-10 had an AUC of 924.41, while its Fab counterpart had an AUC of 57.16. More rapid clearance of the antibody fragment was also observed, albeit somewhat less dramatically, when PE was conjugated to whole antibody and the Fab fragment thereof. HSA conjugated to the Fab fragment targeting moiety resulted in a dramatically increased AUC of from 57.16 (NR-LU-10(Fab) to 881.61 (NR-LU-10(Fab):HSA). As this data would suggest, conjugation of HSA to a NR-LU-10(Fab):PE conjugate increased the AUC of the immunoactive agent over that of that conjugate alone (117.32 to 160.67).

Serum half-life measurements designated alpha phase and beta phase represent two phases of serum half-life calculated from AUC measurements at different time intervals. The alpha measurement represents serum half-life at a relatively short initial time interval, while the beta measurement is indicative of serum half-life of the material tested for a longer, later time interval. Alpha half-life is typically characterized by a rapid reduction in serum concentration of administered materials immediately following such administration. Beta half-life is typically characterized by more gradual reduction in serum concentration over a longer time interval following administration.

TABLE 2

| | Serum Half-life | |
|---|---|---|
| Material Tested | Alpha | Beta |
| NR-LU-10(Fab):PE | 0.06 | 1.53 |
| NR-LU-10(Fab):PE:HSA | 0.39 | 4.11 |

As shown in Table 2, the increase in the serum half-life during the alpha phase for immunoconjugates according to the present invention was on the order of a 6-fold increase, while the increase in the serum half-life during the beta phase was on the order of about 2.5-fold. That is, the serum concentration of conjugates comprising HSA was much higher than that of the corresponding immunoconjugates alone during both the alpha and beta phases. Moreover, significantly more immunoactive agent was present in vivo during the important initial stages following administration. As a result, a greater amount of administered immunoactive agent remained in vivo for the commencement of the beta phase. The beta phase is both longer and features more gradual reduction in serum concentration of administered molecules, and the total serum half-life of the immunoactive agent was significantly enhanced.

EXAMPLE VI

Toxicology Studies with MAb:PE:HSA Conjugates

Toxicology studies were performed in non-tumor bearing Balb/C female mice weighing about 20–25 gm. Various conjugates were produced using the thioether linkage protocol described above in Examples I, II and III and were injected intraperitoneally in a volume of 0.5 ml. Control mice received 0.5 ml PBS containing 1 mg HSA/ml. Mice were observed for signs of toxicity daily for 14 days. The results are shown in Table 3.

TABLE 3

| Hybrid Molecule | Dose-μg/mouse | # Deaths/# Treated |
|---|---|---|
| Control (HSA/PBS) | 500 μg | 0/5 |
| NR-LU-10:PE$_{ref}$(8.5) | 5 μg | 0/5 |
| | 10 μg | 4/5 |
| | 25 μg | 5/5 |
| NR-LU-10:PE$_{ref}$(7.5) | 50 μg | 4/5 |
| NR-LU-10:PE$_{ref}$:HSA | 10 μg | 0/5 |
| | 25 μg | 0/5 |
| | 50 μg | 2/5 |
| NR-LU-10:PE$_{ref}$:HSA (DTNB) | 10 μg | 0/5 |
| | 25 μg | 2/5 |
| | 50 μg | 4/5 |

As shown in Table 3, linkage of HSA to immunoconjugates according to the present invention results in reduced toxicity compared to that of the conjugate alone. Fewer deaths were recorded at higher dosage rates for conjugates comprising HSA.

Additional toxicology studies were conducted substantially as described above using conjugates similar to those tested above, but having thioether or disulfide bonds at the PE$_{ref}$:HSA linkage. Table 4 shows the toxicology results for thioether and disulfide linkages. As the results shown in Table 4 indicate, thioether-linked conjugates exhibited far less toxicity than their disulfide-linked counterparts.

TABLE 4

| Hybrid Molecule | Dose-μg/mouse | #Deaths/#Treated |
|---|---|---|
| Control (HSA/PBS) | 500 μg | 0/5 |
| Thioether Linkage | 10 μg | 0/5 |
| Disulfide Linkage | 10 μg | 4/5 |

EXAMPLE VII

Cytotoxicity of NR-LU-10:PE Conjugates

Cytotoxicity of conjugates prepared in accordance with the thioether linkage protocol outlined in Examples I, II and III was studied. Each conjugate tested was exposed to antigen-positive HT29 colon cells and antigen-negative M14-melanoma cells for 24 hours. The target cells were washed, and levels of protein synthesis (as measured by $^{14}$C-leucine incorporation) by target cells exposed to each test molecule were compared.

The ID$_{50}$ of the NR-LU-10(Fab):PE:HSA conjugate for antigen-positive HT29 cells was approximately 4 ng/ml, while that of NR-LU-10(Fab):PE was approximately 0.7 ng/ml and that of HSA:PE was several orders of magnitude higher. In contrast, the ID$_{50}$ of NR-LU-10(Fab):PE:HSA was approximately 1 μg/ml with respect to antigen-negative M14 cells, compared to approximately 50 ng/ml for NR-LU-10(Fab):PE, and at least one order of magnitude higher for HSA:PE.

NR-LU-10(Fab):PE immunoconjugates exhibited higher cytotoxicity for both antigen positive and antigen negative cells than the conjugates comprising HSA coupled to the corresponding immunoconjugates. Both the conjugates exhibit selectivity for antigen positive cells. However, NR-LU-10(Fab):PE:HSA conjugates exhibited greater selectivity for antigen positive cells than the immunoconjugate alone. Thus, conjugates of the present invention comprising HSA moieties are both potent and selective.

EXAMPLE VIII

Cytotoxicity of NR-LU-10:Refolded PE Conjugates

Cytotoxicity of conjugates comprising NR-LU-10:PE$_{ref}$:HSA was compared to that of PE. The conjugates tested were prepared in accordance with the thioether linkage protocol outlined in Examples I, II and III. Each conjugate tested had a Mab:PE molar ratio of approximately 1:1.

The test samples, including conjugates and PE, were exposed to antigen-positive HT29 colon cells and antigen-negative M14-melanoma cells for 24 hours. The target cells were washed, and levels of protein synthesis (as measured by $^{14}$C-leucine incorporation) by target cells exposed to the conjugates and PE were compared.

Results revealed that the ID$_{50}$ of the NR-LU-10:PE$_{ref}$:HSA conjugate for antigen-positive HT29 cells ranged from approximately 1.4 ng/ml to approximately 1.8 ng/ml, while that of PE was approximately 2.0 ng/ml. In contrast, the ID$_{50}$ of PE was approximately 1.8 ng/ml in assays against antigen-negative M14-cells, while that of the NR-LU-10:PE$_{ref}$:HSA conjugates tested were at least one order of magnitude higher, with no appreciable increase in cytotoxicity over baseline values. These data demonstrate that PE is cytotoxic to both antigen positive and antigen negative cells, with very little selectivity therebetween. Conjugates comprising NR-LU-10:PE$_{ref}$:HSA are both potent and selective for antigen positive cells.

The cytotoxicity of conjugates described above as NR-LU-10:HSA:PE$_{ref}$, but additionally stabilized with DTNB, was measured substantially as described above. The stabilized conjugate (NR-LU-10:PE$_{ref}$-HSA(DTNB), a NR-LU-10:PE immunoconjugate, and PE were exposed to antigen-positive positive HT29 colon cells and antigen-negative M14-melanoma malenoma cells for 24 hours. The target cells were washed, and levels of protein synthesis (as measured by $^{14}$C-leucine incorporation) by target cells exposed to the stabilized conjugate, immunoconjugate and PE were compared.

Cytotoxicity assays revealed that the ID$_{50}$ of the NR-LU-10:PE$_{ref}$:HSA(DTNB) conjugate for antigen-positive positive HT29 cells ranged from approximately 0.7 ng/ml to approximately 1.4 ng/ml, while that of PE alone was approximately 1.5 ng/ml. NR-LU-10:PE was extremely cytotoxic, even at very low concentration levels. In contrast, the ID$_{50}$ of PE was approximately 2.7 ng/ml in assays against antigen-negative M14-cells while that of the NR-LU-10:PE$_{ref}$:HSA(DTNB) conjugates tested were at least one order of magnitude higher, with no appreciable increase in cytotoxicity over baseline values at 3 ng/ml, the highest concentration measured. The NR-LU-10:PE immunoconjugates exhibited an ID$_{50}$ of approximately 0.7 ng/ml.

These data demonstrate that PE alone is cytotoxic to both antigen positive and antigen negative cells, with relatively little selectivity therebetween. NR-LU-10:PE is highly cytotoxic for both antigen positive and antigen negative cells, but exhibits selectivity for antigen positive cells. NR-LU-10:PE$_{ref}$:HSA(DTNB) conjugates are both potent and more highly selective for antigen positive cells than the NR-LU-10:PE immunoconjugates alone.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A conjugate of a proteinaceous toxin, targeting moiety and albumin moiety wherein:
   a proteinaceous toxin selected from the group consisting of: ricin; abrin; diphtheria toxin; Pseudomonas exotoxin A; and modified forms thereof that exhibit toxic properties that are substantially equivalent to those of a native form of the corresponding proteinaceous toxin;
   a targeting moiety linked to said proteinaceous toxin, said targeting moiety selected from the group consisting of: antibodies; antibody fragments; and modified antibodies and fragments having binding activities substantially equivalent to that of a native form of the corresponding antibody or fragment; and
   an albumin moiety linked to one of said targeting moiety and said proteinaceous toxin wherein the molar ratio of targeting moiety:proteinaceous toxin:albumin moiety is about 1:1:1 to 2.

2. A conjugate according to claim 1, wherein said proteinaceous toxin comprises Pseudomonas exotoxin A (PE), modified forms thereof, or therapeutically active fragments thereof that exhibit toxic properties that are substantially equivalent to those of a native form of PE.

3. A conjugate according to claim 1, having a molar ratio of approximately 1:1:1, targeting moiety:proteinaceous toxin:albumin moiety.

4. A conjugate according to claim 1, wherein said albumin moiety is linked to said proteinaceous toxin.

5. A conjugate according to claim 1, wherein said albumin moiety is linked to said targeting moiety.

6. A conjugate according to claim 1, wherein an albumin moiety is linked to both said targeting moiety and said active moiety.

7. A conjugate according to claim 1, wherein said antibody fragment is selected from the group consisting of: Fab; Fab'; F(ab')$_2$; Fv; and single chain antibody fragments.

8. A conjugate according to claim 1, wherein said albumin moiety is linked to said proteinaceous toxin by means of a thioether linkage.

9. A conjugate according to claim 8, wherein said targeting moiety is linked to said proteinaceous toxin by means of a thioether linkage.

10. A conjugate according to claim 1 of:
a proteinaceous toxin selected from the group consisting of: diphtheria toxin; Pseudomonas exotoxin A; inactivating proteins; and combinations and modified forms thereof that exhibit toxic properties that are substantially equivalent to those of a native form of the corresponding proteinaceous toxin;
a targeting moiety linked to said proteinaceous toxin, said targeting moiety selected from the group consisting of: antibodies; antibody fragments; and modified antibodies and fragments having binding activities substantially equivalent to that of a native form of the corresponding antibody or fragment; and
an albumin moiety linked to at least one of said targeting moiety and said proteinaceous toxin
there should be no fee for the above amendment, since the number of claims has been reduced.

* * * * *

UNITED STATES PATENT AND TRADEMARK OFFICE
CERTIFICATE OF CORRECTION

PATENT NO. : 5,116,944
DATED : May 26, 1992
INVENTOR(S) : Gowsala P. Sivam and A. Charles Morgan It is certified that error appears in the above-identified patent and that said Letters Patent is hereby corrected as shown below:

Column 2, line 10, change "Pseudomonas" to --*Pseudomonas*--.

Column 3, line 26, change "in vivo" to --*in vivo*--.

Column 5, line 56, change "Pseudomonas" to --*Pseudomonas*--.

Column 6, line 29, change "NR-LU-IO" to --NR-LU-10--.

Column 6, line 50, change "TM-AM-hSA" to --TM-AM-HSA--.

Column 7, line 6, change "p-reserve" to --preserve--.

Column 7, line 40, after "comprises" insert --reacting a proteinaceous active moiety with a--.

Column 7, line 63, change "76:1261" to --*76:1261*--.

Column 8, line 58, change "76:1261" to --*76:1261*--.

Column 8, line 60, change "Pseudomonas" to --*Pseudomonas*--.

Column 9, line 15, after "mixtures" delete "-1".

Column 10, line 29, change "With" to --with--.

Column 10, line 42, after "4°C" delete ".".

Column 12, lines 27 and 30, change "in vivo" to --*in vivo*--.

Column 14, line 50, claim 1, line 1, after "of" insert --:-- and line break.

Column 14, line 65, claim 1, line 20, after "to" insert --at least--.

Column 15, line 20, claim 6, line 3, change "active moiety" to --proteinaceous toxin--.

UNITED STATES PATENT AND TRADEMARK OFFICE
CERTIFICATE OF CORRECTION

PATENT NO. : 5,116,944

DATED : May 26, 1992

INVENTOR(S) : Gowsala P. Sivam and A. Charles Morgan

It is certified that error appears in the above-identified patent and that said Letters Patent is hereby corrected as shown below:

Column 16, line 10, claim 10, line 4, after "A;" delete "inactivating proteins, and combinations".

Column 16, line 22, claim 10, line 16, after "toxin" insert --.-- and delete "there should be no fee for the above amendment since the number of claims has been reduced".

Signed and Sealed this

Eighteenth Day of October, 1994

Attest:

BRUCE LEHMAN

*Attesting Officer*     *Commissioner of Patents and Trademarks*